United States Patent
Rosiello et al.

(10) Patent No.: US 10,842,756 B2
(45) Date of Patent: Nov. 24, 2020

(54) NANOPARTICLES, COMPOSITION AND SYSTEM FOR DELIVERING 5FU AND USES THEREOF

(71) Applicant: BIOVIIIX S.R.L., Naples (IT)

(72) Inventors: Davide Rosiello, Naples (IT); Vincenzo Vigilanza, Andria (IT); Salvatore Asero, Misterbianco (IT); Matteo Di Minno, Naples (IT); Roberta Lupoli, Naples (IT)

(73) Assignee: BIOVIIIX S.R.L., Naples (IT)

( * ) Notice: Subject to any disclaimer, the term of this patent is extended or adjusted under 35 U.S.C. 154(b) by 157 days.

(21) Appl. No.: 15/767,001

(22) PCT Filed: Oct. 9, 2015

(86) PCT No.: PCT/IT2015/000253
§ 371 (c)(1),
(2) Date: Apr. 9, 2018

(87) PCT Pub. No.: WO2017/060929
PCT Pub. Date: Apr. 13, 2017

(65) Prior Publication Data
US 2018/0289627 A1    Oct. 11, 2018

(51) Int. Cl.
| | |
|---|---|
| *A61K 9/51* | (2006.01) |
| *A61K 47/42* | (2017.01) |
| *A61P 35/00* | (2006.01) |
| *A61K 45/06* | (2006.01) |
| *A61K 9/00* | (2006.01) |
| *A61L 9/14* | (2006.01) |
| *A61K 9/16* | (2006.01) |
| *A61K 31/513* | (2006.01) |

(Continued)

(52) U.S. Cl.
CPC .......... *A61K 9/5169* (2013.01); *A61K 9/0019* (2013.01); *A61K 9/146* (2013.01); *A61K 9/1658* (2013.01); *A61K 31/513* (2013.01); *A61K 45/06* (2013.01); *A61K 47/42* (2013.01); *A61P 35/00* (2018.01); *A61K 2300/00* (2013.01); *B82Y 5/00* (2013.01)

(58) Field of Classification Search
CPC ...... A61K 9/5169; A61K 47/42; A61K 45/06; A61K 9/0019; A61K 9/146; A61K 9/1658; A61K 31/513; A61K 2300/00; A61P 35/00; B82Y 5/00
See application file for complete search history.

(56) References Cited

PUBLICATIONS

Wilson et al., Nanoparticles based on albumin: Preparation, characterization and the use for 5-flurouracil delivery, International Journal of Biological Macromolecules, vol. 51, 874-878, 2012.

(Continued)

*Primary Examiner* — Trevor Love
(74) *Attorney, Agent, or Firm* — Meunier Carlin & Curfman LLC

(57) ABSTRACT

The present invention relates to nanoparticles of albumin loaded with 5FU and/or with a precursor thereof. Further, the present invention relates to a pharmaceutical composition or a 5FU delivery system and/or a precursor thereof comprising nanoparticles. The present invention also relates to a method for producing said nanoparticles and the use of the nanoparticles, the pharmaceutical composition or the 5FU delivery system and/or a precursor thereof as a medicament, in particular for use in treatment of tumours.

10 Claims, 3 Drawing Sheets

(51) Int. Cl.
*B82Y 5/00* (2011.01)
*A61K 9/14* (2006.01)

(56) References Cited

PUBLICATIONS

Mallamma et al., Formulation and evaluation of 5-flurouracil Loaded HSA Nanoparticle for Controlled Drug Delivery, International Journal of Advanced Research, vol. 7:6, 23-30, 2013.
International Search Report and Written Opinion dated Aug. 2, 2016, from International Application No. PCT/IT2015/000253, 19 pages.
Morimoto, Y. et al. "Drug-Carrier Property of Albumin Microspheres in Chemotherapy. IV Antitumor Effect of Single-shot or Multiple-shot Administration of Microsphere-entrapped 5-Fluorouracil on Ehrlich Ascites or Solid Tumor in Mice", Chem. Pharm. Bull. 28(10) 3087-3092 (1980), XP-001094117.
Maghsoudi, A. et al. "5-Fluorouracil-Loaded BSA Nanoparticles: Formulation Optimization and In Vitro Release Study", AAPS PharmSciTech, vol. 9, No. 4, Dec. 2008 pp. 1092-1096.
Santhi, K. et al. "A Study on the Preparation and Anti-Tumor Efficacy of Bovine Serum Albumin Nanospheres Containing 5-Fluorouracil", Drug Development and Industrial Pharmacy, vol. 28, No. 9, pp. 1171-1179, 2002.

NANOPARTICLES, COMPOSITION AND SYSTEM FOR DELIVERING 5FU AND USES THEREOF

TECHNICAL FIELD

The present invention relates to nanoparticles of albumin loaded with 5FU and/or with a precursor thereof. Further, the present invention relates to a pharmaceutical composition or a 5FU delivery system and/or a precursor thereof comprising said nanoparticles.

The present invention also relates to a method for producing said nanoparticles and the use of said nanoparticles, said pharmaceutical composition or said 5FU delivery system and/or a precursor thereof as a medicament, in particular for use in treatment of tumours.

PRIOR ART 5-fluorouracil (5FU) and its oral prodrug, capacitabine, are among the antineoplastic drugs most commonly prescribed for treatment of tumours. Especially treated with 5FU are tumours of the gastro-intestinal tract, the breast, the head and the neck.

The effectiveness and collateral effects associated to administration of 5FU show an intra- and inter-individual variability. The pharmacokinetic variability (PK) of 5FU has been associated to various factors, such as for example age, gender, state of the disease and function of the organs.

In particular, it has recently been demonstrated that the activity of the catabolic enzyme dihydropyrimidine dehydrogenase (DPD) is among the main factors able to influence the pharmacokinesis of 5FU. In fact, subjects lacking in DPD have shown a multi-visceral toxicity which in some cases has led to death following the 5FU treatment.

5FU is characterised by a low therapeutic index and the therapeutic drug monitoring (TDM) of 5FU (adoption of the dose on the basis of PK/PD data) has demonstrated beneficial effects, mitigating the consequences of non-optimal dosage or over-exposure to 5FU.

The adverse effects of 5FU are programme-dependent, for example myelotoxicity is the principal toxic effect of a 5FU administration in bolus, while the hand-foot syndrome, stomatitis, neuro- and cardiotoxicity are mainly associated to continuous infusions. At present, continuous 5FU infusion is preferable to administration in bolus for questions of safety and pharmacodynamics.

Numerous efforts have been made to overcome 5FU toxicity, for example the development of prodrugs. However, the variability intra- and inter-patient of the pharmacokinetic parameters have given rise to safety problems and the need for a pharmaceutical monitoring (TDM) correlated to the assumption of these compounds.

Thus, still today, there is a need to improve the pharmacokinetic and pharmacodynamic properties (PK/PD) of 5FU. In particular, there is a need for new 5FU formulations which enable a drug release that is target-specific and controlled.

In the attempt to overcome these difficulties various systems have been researched and produced which enable modulation of the 5FU delivery, for example systems based on the use of microspheres, liposomes and nanoparticles. Recently 5FU has been formulated encapsulated in nanoparticles of zein, which however is a specific formulation only for hepatic drug delivery.

Therefore the need is still greatly felt for development of 5fU delivery systems, in particular suitable for administering the drug parenterally, which are able to guarantee release of constant therapeutic concentrations of the 5FU drug without having recourse to repeated administrations or slow infusions.

The above-reported needs have been resolved by the Applicant with 5FU loaded albumin nanoparticles and/or a precursor thereof, or with a pharmaceutical composition or a delivery system comprising the loaded nanoparticles where the nanoparticles are characterised by a mean diameter that is smaller than 200-220 nm and are able to release, in a constant and prolonged way over time, therapeutically effective doses of drug. Further, thanks to their small dimensions, they are effectively administered parenterally, in particular for treatment of tumours.

The present invention also relates to a method for preparing the 5FU loaded nanoparticles and/or precursors thereof, which comprises the following steps: preparing an albumin and drug solution, desolvating the solution with a drop-by-drop added solvent, sonicating the desolvated solution, inducing cross-linking, isolating the nanoparticles obtained and possibly lyophilising them.

The nanoparticles or the pharmaceutical composition/delivery system of the present invention are advantageously very stable as demonstrated by the high measured zeta potential values. Further, they show a low polydispersity index and are therefore monodispersed and homogeneous systems, i.e. each nanoparticle of the system/composition has of average the same dimensions. The nanoparticles or the pharmaceutical composition/delivery system of the present invention therefore contain and release constant quantities of drug over a prolonged period. Lastly, nanoparticles have dimensions of less than 200-220 nm and therefore show to be an ideal system for administrating by parenteral infusion of 5FU and/or its precursors.

BRIEF DESCRIPTION OF THE FIGURES

The present invention will be described in detail in the following even with the aid of the appended figures, in which.

DETAILED DESCRIPTION OF THE INVENTION

Figure 1:
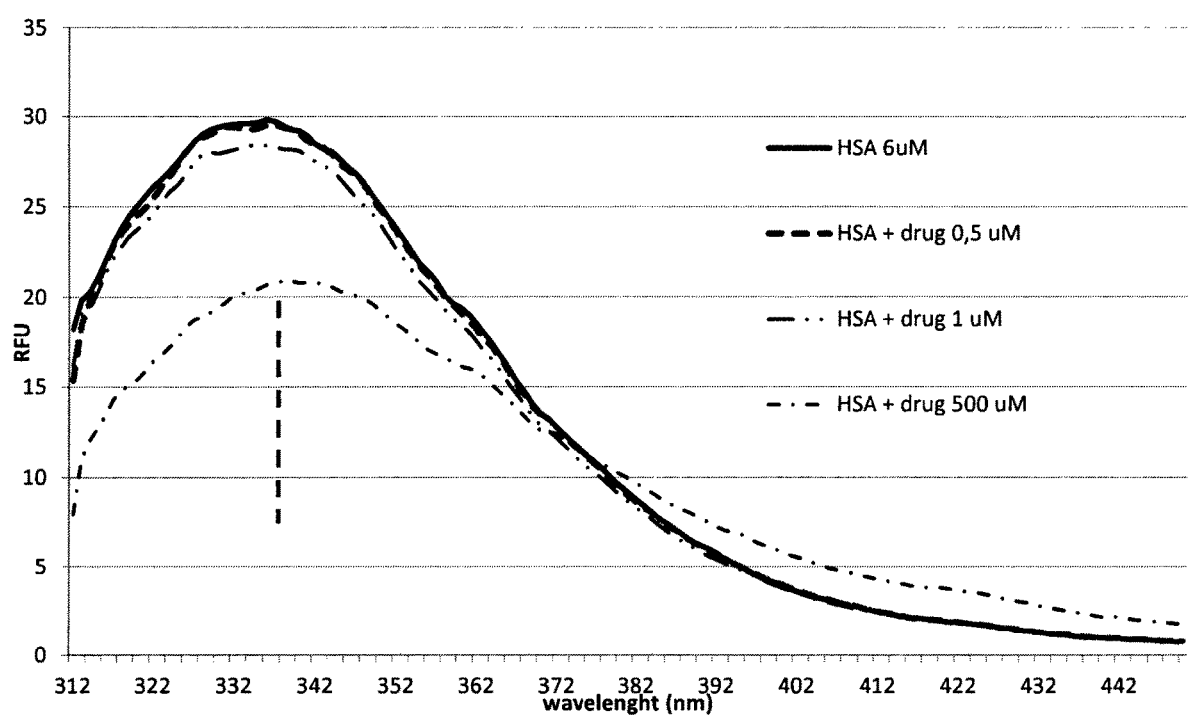
FIG. 1 shows the results of the fluorescence quenching studies of the following solutions: HSA (Human Serum Albumin) 6 μM; HSA 6 μM+5FU 0.5 μM; HSA 6 μM+5FU 1 μM, and HSA 6 μM+5FU 500 μM.

A first aspect of the present invention relates to albumin nanoparticles loaded with a quantity of 5FU and/or a precursor thereof, variable from 10 to 500 μg/ml, preferably from 50 to 250 μg/ml. More preferably the quantity of 5FU and/or the precursor thereof into the albumin nanoparticles varies from 70 to 200 μg/ml, more preferably from 150 to 200 μg/ml.

The nanoparticles of the present invention are characterised by an average diameter of the particles preferably varying from 50 to 220 nm, more preferably from 80 to 180 nm, still more preferably from 100 to 150 nm, still more preferably from 110 to 130 nm, still more preferably the diameter is about 120 nm.

The average diameter of the particles, i.e. the average dimension of the particles, is also indicated as Z-ave. It is a very important parameter, in particular for the parenteral administration of drugs, such as those having an anti-tumorous action such as 5FU and/or precursors thereof.

In the context of the present invention, by parenteral administration is meant intra-vascular (intravenous, for example via bolus, or intra-arterial) intramuscular or cutaneous (subcutaneous or intradermic).

A further aspect of the present invention relates to a pharmaceutical composition comprising the nanoparticles described in the foregoing and accepted pharmaceutical excipients.

A further aspect of the present invention relates to a delivery (or transport) system of the 5FU and/or precursors thereof comprising the nanoparticles or the pharmaceutical composition of the present invention. Therefore a further aspect of the present invention relates to use of the nanoparticles or the pharmaceutical composition of the present invention as a delivery system of 5FU and/or precursors thereof. In particular, the delivery of the drug is, preferably, a constant delivery of therapeutically effective doses of drug. Further, the delivery is preferably site-specific and preferably relates to tumorous zones.

In some embodiments the weighted ratio between said 5FU and/or a precursor thereof and said albumin varies preferably from 0.005 to 4; more preferably from 0.01 to 1, still more preferably from 0.025 to 0.8, still more preferably from 0.05 to 0.4, still more preferably about 0.2. In other words the w/w % 5FU and/or the precursor/albumin of the nanoparticles/pharmaceutical composition/delivery system varies from 0.5 a 400; more preferably from 1 to 100, still more preferably from 2.5 to 80, still more preferably from 5 to 40, still more preferably about 20.

Advantageously, the nanoparticles/pharmaceutical composition/delivery system of the present invention are very stable. In fact, they have a zeta potential that varies preferably from 20 to 80 mV, preferably from 30 to 60 mV, even more preferably from 35 to 50 mV.

In the context of the present invention, by zeta potential is meant the electrical potential which is between the means of dispersion of the nanoparticles and the double electrical layer of solvation of the nanoparticles. The zeta potential is an index of the stability (i.e. lower tendency to coalescence) of the nanoparticles. Generally a potential of between 30 and 40 mV is an index of a moderate stability. A potential of between 40 and 60 mV is an index of good stability.

Advantageously, the nanoparticles/pharmaceutical composition/delivery system of the present invention are also a very homogeneous system and consequently of high-quality. In fact they have a polydispersity index which preferably varies from 0.01 to 1; more preferably from 0.05 to 0.5, still more preferably from 0.07 to 0.3.

The polydispersity index, or PDI, is a parameter which takes account of the dimensional distribution of the nanoparticles. The lower the PDI, the more homogeneous is the sample.

In a preferred embodiment of the invention, the precursor of 5FU is selected from among: capecitabine, UFT, S-1, dihydropyrimidine dehydrogenase inhibitors and folic acid.

In a further preferred embodiment of the invention, the albumin can be the whole protein or fragments thereof. It is preferably human, in particular extracted from serum, preferably human. It is preferably characterised by a molecular weight varying from 50000-100000 Da, preferably 60000-70000 Da.

The albumin used for the present invention is preferably extracted according to the EC regulated procedures, i.e. in GMP and is preferably negative to at least one of the following proteins: hepatitis B (HBsAg), and/or antivirus antibodies of human immunodeficiency (HIV), and/or hepatitis C antivirus antibodies (HCV). The albumin of the present invention is preferably equipped with Plasma Master File.

A further aspect of the present invention relates to the nanoparticles/pharmaceutical composition/delivery system for use as a medicament.

A further aspect of the present invention relates to the nanoparticles/pharmaceutical composition/delivery system for use in the treatment of tumours.

Parenteral administration of 5FU and/or precursors thereof for medical use is preferably advised, preferably intravascular, more preferably intravenous, preferably by means of bolus, or intra-arterial.

Alternatively administration is intra-muscular or cutaneous, preferably subcutaneous or intradermic.

The nanoparticles/pharmaceutical composition/delivery system of the present invention preferably enable a constant release of the 5FU and/or the precursor thereof that is about 10% of the quantity of drug initially loaded. The release preferably continues for up to 24 hours or more, preferably when it is administered parenterally. In other words, the efficiency of release of the nanoparticles/pharmaceutical composition/delivery system of the present invention is about 10% of the quantity of loaded drug.

The quantities of drug released constantly by the nanoparticles/pharmaceutical composition/delivery system of the present invention are about 10-50 µg/ml, preferably 15-30 µg/ml, more preferably 17-22 µg/ml.

The tumours which are preferably treatable with nanoparticles or the pharmaceutical composition or delivery system of 5FU of the present invention are selected from among: colon carcinoma, rectal carcinoma, gastric adenocarcinoma, head/neck tumour, hepatic carcinoma, pancreatic carcinoma, peritoneal carcinomatosis, oesophageal carcinoma, breast carcinoma, ovarian carcinoma, microcytoma lung tumour, non-microcytoma lung tumour, non-invasive surface carcinoma of the bladder, Kaposi's sarcoma, and sarcoma of the soft tissues, preferably the tumour being selected from among: colon carcinoma, rectal carcinoma, gastric adenocarcinoma, pancreatic carcinoma, breast carcinoma, microcytoma lung tumour, non-microcytoma lung tumour, non-invasive surface carcinoma of the bladder.

In a preferred embodiment of the invention the nanoparticles or a pharmaceutical composition or a system for transporting 5FU of the present invention can be administered in combination with at least a chemotherapy agent, and/or with radiotherapy, and/or with surgery.

A further embodiment of the invention relates to a method for treating tumours which comprises steps of administering to a patient a therapeutically effective quantity of 5FU-loaded nanoparticles and/or a precursor thereof or with a composition or a delivery system comprising said nanoparticles, the nanoparticles/pharmaceutical composition being characterised as described in the foregoing. The tumours treated are preferably the ones mentioned in the foregoing.

A further preferred aspect of the present invention relates to a method for the production of nanoparticles comprising albumin and 5FU and/or a precursor thereof, comprising the steps of:

(i) preparing a solution, preferably aqueous, of albumin and 5FU and/or a precursor thereof;
(ii) adding to the aqueous solution obtained by the step (i) an organic solvent, preferably alcoholic, more preferably ethanol, drop by drop, preferably under stirring (dripping step);
(iii) sonicating the composition obtained by step (ii);
(iv) inducing cross-linking, preferably with addition of glutaraldehyde; and, possibly
(v) isolating the nanoparticles obtained from step (ii) preferably by centrifugation/ultracentrifugation.

The method of the present invention can alternatively be defined also as a method for production of nanoparticles of albumin loaded with 5FU and/or with a precursor thereof.

The albumin and the 5FU and/or a precursor thereof are preferably present in the solution according to step (i) in a w/w % ratio of 5FU/albumin which preferably varies from 2.5 to 60, more preferably from 5 to 40. The solution has a pH that is variable preferably from 8 to 10, more preferably from 8.5 to 9, even more preferably is about 8.6.

The two components according to step (i) are preferably left to react for a time ranging preferably from 1 to 72 hours, more preferably from 1 to 48, still more preferably for about 24 hours.

In a preferred embodiment of the invention, step (i) is realised at about 25° C. and at about 600 rpm.

In a further preferred embodiment of the invention, the quantity of solvent added in step (ii) depends on the pH of the solution of step (i).

Step (ii) preferably occurs at a dripping velocity of about 0.5-2 ml/minute, preferably about 1 ml/minute.

In a preferred embodiment of the invention, step (iii) is realised for 5-10 minutes, preferably about 5 minutes, at about 25° C. and about 600 rpm.

In a preferred embodiment of the invention, the quantity of cross-linker of step (iv), preferably glutaraldehyde, with respect to the albumin, varies from 50 to 150 per mg of albumin, more preferably from 80 to 120 mg per mg of albumin, still more preferably from 90 to 100 mg per mg of albumin, still more preferably is about 94 mg per mg of albumin.

As an alternative to glutaraldehyde it is possible to use as crosslinker UV irradiation, possibly in the presence of a polyalcohol such as glucose, mannose or erythrose, at a concentration which varies preferably between 1 and 10 mM, or the cross-linking is made via disulphide bridges.

In a preferred embodiment of the invention, the centrifugation/ultracentrifugation of step (v) is preferably realised at about 10000 rpm for a time which is preferably about 10-15 minutes at a temperature which is preferably about 10° C.

In a preferred embodiment of the invention, it is advisable to adjust the pH of the solution with NaOH, preferably NaOH 0.01 M.

Possibly after step (iv) or (v) the loaded nanoparticles or the pharmaceutical composition or the delivery system containing the loaded nanoparticles can be lyophilised.

The lyophilising step is preferably done by re-suspending the isolated nanoparticles, preferably by centrifugation/ultracentrifugation, in a saline solution such as PBS, with a neutral pH, preferably at a pH which varies between 7-7.6, more preferably the pH is about 7.4.

A cryoprotectant is preferably added to the saline solution, for example glucose, trehalose, mannitol, sucrose, erythrose or beta-cyclodextrin, preferably hydroxypropyl-beta-cyclodextrin. The concentration of the cryoprotectant is preferably variable from 1 to 10%.

Then the solution is frozen, preferably at about −20° C. and then lyophilised.

A further aspect of the present invention relates to nanoparticles obtained/obtainable with the method according to the present invention or a pharmaceutical composition or delivery system of 5FU and/or precursors thereof comprising the nanoparticles obtained in this way.

Said nanoparticles are characterised by an average diameter of the particles preferably varying from 50 to 220 nm, more preferably from 80 to 180 nm, still more preferably from 100 to 150 nm, still more preferably from 110 to 130 nm, still more preferably the average diameter of the particles is about 120 nm.

The nanoparticles of the present invention are preferably loaded with the drug with an efficiency varying between 5-40%, preferably between 7-20%. In terms of loaded drug, considering the weighted ratios of albumin and drug described in the foregoing, this means a quantity of drug varying from 10 to 500 μg/ml, preferably from 50 to 250 μg/ml. More preferably the quantity of 5FU and/or the precursor thereof varies from 70 to 200 μg/ml, still more preferably from 150 to 200 μg/ml.

The nanoparticles/pharmaceutical composition/delivery system of the present invention enable a constant release of the 5FU and/or the precursor thereof that is preferably about 10% of the quantity of drug initially loaded. The release preferably continues for up to 24 hours or more, preferably when it is administered parenterally. In other words, the efficiency of release of the nanoparticles/pharmaceutical composition/delivery system of the present invention is about 10% of the quantity of loaded drug.

The quantities of drug released constantly by the nanoparticles/pharmaceutical composition/delivery system of the present invention are about 10-50 μg/ml, preferably 15-30 μg/ml, more preferably 17-22 μg/ml.

Example

Studies of the 5FU-HSA Bond

HSA is a globular protein which has various binding sites. The majority of molecules bonds to two sites, called site I (sub-domain IIA) and site II (sub-domain IIIA).

In Bertucci et. al, it is demonstrated that the 5FU preferentially bonds to site I of the albumin. To deepen the small amount of data available in the literature, in-silico and chemical-physical evaluation of the 5FU bond with human serum albumin was made.

—In Silico

The computational analysis of the 5FU-HSA bond was made by molecular docking, using as forecasting software Autodock 4.2 and FRED (OpenEyescientific software).

In general molecular docking studies enable a forecasting of the bonding modes of the compounds to their targets. Bonding modes are technically knows as poses, each pose being associated to a docking score. More specifically, the bind is considered more favourable as the score lowers (i.e. is more negative).

The 3D structure of HSA was obtained by a query at site pdb.org (Protein Data Bank) and the PDB structure was used: 2BXF with no ligand present. The 5FU, aspirin and paclitaxel structure files were obtained from pubchem.ncbi.nlm.nih.gov.

Blind docking of the 5FU was first carried out, not considering any particular HSA site. In fact, blind docking is an approximated procedure since molecular docking occurs over the whole pharmacological target. As regards the 5-FU, the majority of the pose is localised in site I (sub-domain IIA).

Subsequently a more precise calculation was carried out, focalising the 5FU docking in sub-domain IIA. The calculation was initially carried out with Autodock 4.2 and subsequently with FRED.

—Chemical-Physical Characterisation.

The HSA fatty (acid free Sigma Aldrich©) and the 5FU (analytic grade Sigma Aldrich) were solubilised in PBS at pH 7.2 for the preparation of the stock solutions (Albumin 60 uM, 5FU 10 mM, 1 mM, 10 uM). The stock solutions were conserved at 4° C. in amber glass vials, following the modalities indicated by the supplier.

The analyte solutions were prepared in wells of a black FluoroNuncThermoscientific© multiwell, up to a maximum volume of 200 ul.

The multiwell was incubated for 12 hours at 4° C., after which the fluorescence was read.

The fluorescence emission spectra were collected using the Varioskan Flash Multireader©: λex=295 nm; bandwidth 5 nm; spectral range 300-440 nm; measurement length=300 ms; instrument temperature 24° C.

The 5FU is not excited at 295 nm and does not fluoresce in the analysed spectral range.

For the 5U a very low fluorescence was detected in the above-mentioned range at higher concentrations (500 uM-relative fluorescence unit RFU=4).

As regards the UV-vis absorbance spectroscopy, the analyte solutions were prepared in wells of a UV-vis-transparent multiwell (multiwell Corning UV-Star©), up to a maximum volume of 200 ul. The UV-vis spectra were collected using the Varioskan Flash Multireader©: bandwidth 5 nm; spectral range 200-440 nm; instrument temperature 24° C.

—Results

The 5FU preferably bonds to site I of the HSA, forming hydrogen bonds with the residues Lys 189, Arg 222, Glu 292 of the HSA. Tryptophan 214 is in proximity of these residues. Fluorescence quenching studies have demonstrated that the 5FU/domain I bond of the HSA occurs.

FIG. 1 shows the fluorescence spectra of the following solutions:

HSA 6 uM;
HSA 6 uM+5-FU 0.5 uM;
HSA 6 uM+5-FU 1 uM
HSA 6 uM+5-FU 500 uM

The results reported in FIG. 1 demonstrate that there is fluorescence quenching on increasing the concentration of the drug. Further, at high 5FU concentrations, there is a bathochromic effect (redshift), which indicates that Trp214 is exposed to a more polar environment (greater exposure to the solvent). This datum is coherent with the fact that the HSA pocket, where the 5FU bonds (in silico datum), it defines a hydrophilic environment.

Further, following the binding with the 5FU, there can be a conformational variation of the HSA, exposing the Trp214 to a more polar environment. Additionally it has been observed that an isosbestic point forms at concentration 500 µM di 5FU, indicating that at this concentration the formation reaction of the 5FU/HSA complex is in equilibrium, i.e. the formation velocity of the complex is equal to that of dissociation.

With the purpose of evaluating whether the quenching of the 5FU is due to a dynamic process, i.e. simple collision of the 5FU with the fluorophore Trp214, or a static process, i.e. formation of a stable 5FU/HSA bond and therefore a stable variation around the Trp214, an analysis was performed of the UV spectrum of the complexes, considering two different molar ratios HSA/5FU (6 µM/1 µM-6 µM/500 µM).

At low 5FU concentrations, the HSA spectrum is not influenced. This indicates that at low concentrations (distant from the equilibrium) an actual HSA/5FU complex is not formed.

Figure 2:
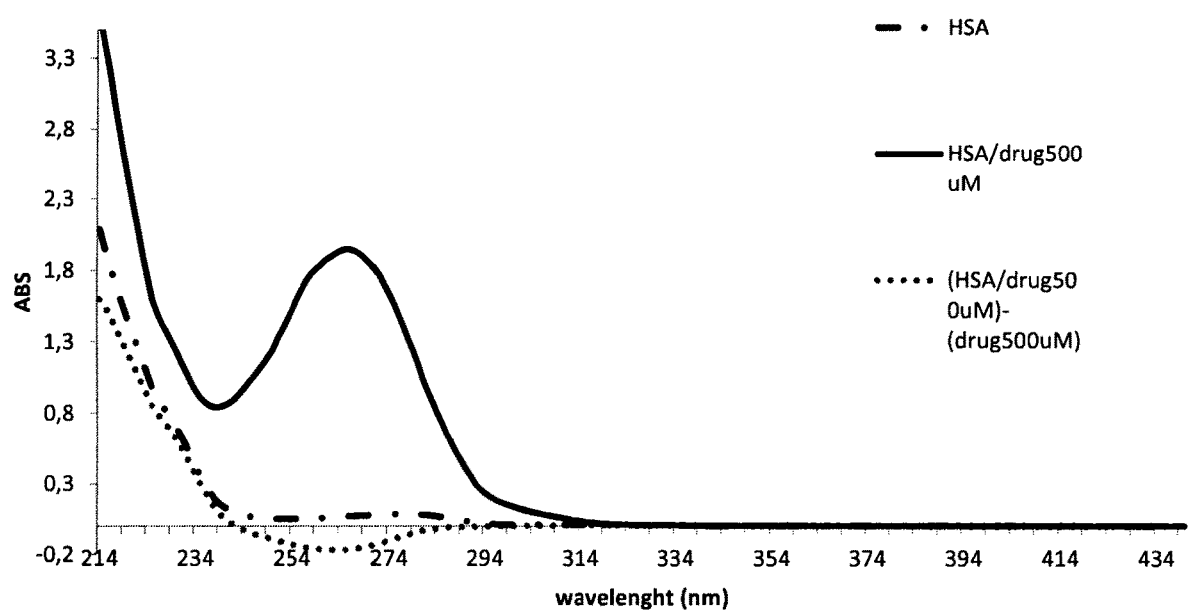
FIG. 2 shows the results of the UV spectrum analysis of the HSA-5FU complex in three molar ratios i.e. HSA+drug 0.501, 1 μM and 500 μM.

On the contrary, at high concentrations, the HSA spectrum is significantly influenced as reported in FIG. 2. This means that the 5FU is bonded stably to the HSA, indicating a static fluorescence quenching.

In conclusion, in silico data and the fluorescence and UV spectroscopy data indicate that a stable 5FU/HSA bond is formed. This binding occurs in the IIA sub-domain, or site I, very possibly inducing a conformational variation of the site, increasing its hydrophilicity (bathochromic effect).

Preparation of the Albumin Nanoparticles

A desolvated solution of albumin was prepared by dissolving 200 mg of Human Serum Albumin (HSA) in 2 millilitres of bi-distilled water (conc. 10% p/v). Thereafter the solution was brought to different pH values with a 0.01 M NaOH solution.

Then 8 millilitres of absolute ethanol were added in the form of drops (the volume of added ethanol is a function of the protein concentration), under stirring at 600 rpm, with the dripping velocity at about 1.0 millilitres per second.

The cross-linking was done by adding 235 microlitres of 8% glutaraldehyde (equivalent to 1.175 microlitres of glutaraldehyde per milligram of HSA). The sample is left in stirring for 24 hours at ambient temperature.

The nanoparticles were isolated by centrifugation at 10000 rpm for 12 minutes at 10° C.

Lastly, the nanoparticles were re-suspended in water and then sonicated for 5 minutes.

The following formula variants were realised, where the variations regarded the pH, the temperature, the ultrasound administration mode, the quantity of glutaraldehyde.

In particular, the tested formulations are summarised in the following table in the Batch column. They were realised in the experimental conditions as in Table I.

TABLE I

| Batch | pH | Temperature | Dripping velocity | Plate stirring (P) 600 rpm/ UT 25 (U) | Volume Glut. (µl) | Sonication (5 minutes) | Sonication mode |
|---|---|---|---|---|---|---|---|
| NP0HSA 1 | 8.6 | room | About 1 ml/min | P | 235 | — | — |
| NP0HSA 2 | 8.6 | room | About 1 ml/min | P | 235 | Pre-glut. | Bath |
| NP0HSA 3 | 8.6 | room | About 1.5 ml/min | P | 235 | Post-glut. | Bath |
| NP0HSA 4 | 8.6 | room | About 1 ml/min | P | 235 | Post crosslinking | Bath |
| NP0HSA 5 | 8.2 | room | About 1 ml/min | P | 235 | Pre-glut. | Probe |
| NP0HSA 6 | 10 | room | About 1 ml/min | P | 235 | Pre-glut. | Probe |

TABLE I-continued

| Batch | pH | Temperature | Dripping velocity | Plate stirring (P) 600 rpm/ UT 25 (U) | Volume Glut. (μl) | Sonication (5 minutes) | Sonication mode |
|---|---|---|---|---|---|---|---|
| NP0HSA 7 | 8.6 | room | About 1 ml/min | P | 235 | Pre-glut. | Bath |
| NP0HSA 8 | 8.6 | 2-3° C. | About 1 ml/min | P | 235 | During EtOH | Bath |
| NP0HSA 9** | 8.6 | room | About 1 ml/min | P | 235 | Pre-glut. | Bath |

—Physical-Chemical Characterisation of the Nanoparticles

The nanocarriers were analysed by means of the Zetasizer Nano ZS 90 which applies the photon-correlation Spectroscopy for determination of the average diameter of the particles (Z-Ave), the poly-dispersion index (PDI) and the zeta potential of the nanoparticles.

The dimensional analysis was conducted using the Dynamic Light Scattering (DLS).

The samples were diluted 1:10 with bi-distilled water to avoid multiscattering phenomena. The data obtained is reported in Table II below.

TABLE II

| Batch | **Z-Ave (nm) | *PDI | Zeta potential (mV) | pH |
|---|---|---|---|---|
| NP0HSA 1 | 167 ± 3.345 | 0.156 ± 0.013 | −50.4 ± 2.51 | 8.6 |
| NP0HSA 2 | 141.2 ± 0.493 | 0.235 ± 0.04 | −43.3 ± 1.10 | 8.6 |
| NP0HSA 3 | — | — | — | 8.6 |
| NP0HSA 4 | 125.4 ± 1.159 | 0.256 ± 0.012 | — | 8.6 |
| NP0HSA 5 | 144.6 ± 3915 | 0.217 ± 0.016 | −46.2 ± 2.0 | 8.2 |
| NP0HSA 6 | 104.4 ± 2.669 | 0.158 ± 0.011 | −48.5 ± 1.6 | 10 |
| NP0HSA 7 | 202.1 ± 12.41 | 0.244 ± 0.003 | −39.2 ± 1.18 | 8.6 |
| NP0HSA 8 | 88.76 ± 6.428 | 0.282 ± 0.012 | — | 8.6 |
| NP0HSA 9 | 109.0 ± 1.909 | 0.182 ± 0.007 | −43.3 ± 1.10 | 8.6 |
| Batch mean 2/9 | 125.45 | 0.208 | −43.3 | — |

As can be noted from the results summarised in the table, the particles obtained have a diameter of less than 200 nm (the mean is 125.45 nm diameter) and therefore this enables the possibility of infusing the nanoparticles (i.v.) in continuous and prolonged infusion.

Incorporation of the Drug

The HSA nanoparticles loaded with 5FU were prepared by incorporating the drug in the protein matrix realised by solubilising the drug with the protein and proceeding to desolvation in order to produce the nanoparticles.

—Incorporating Method During the Desolvating Step

All the steps of the method were conducted out of the light.

The drug (in the quantities reported in Table III) is dissolved together with the HSA in two millilitres of water. Then it is left in stirring at 600 rpm for a variable time (tested 2-24 hours) at 25° C., to enable adsorption of the drug to the protein.

Then the solution pH value is controlled and possibly adjusted with NaOH 0.01 M. Various pH values were tested and the best results were obtained at pH 8.6.

The desolvation then takes place, with about 8 millilitres of ethanol and sonication for 5 minutes in a bath at 25° C. at 600 rpm.

Then the sample is subjected to the step of cross linking (with 235 microlitres of 8% glutaraldehyde.

The nanoparticles obtained are isolated by centrifugation (10000 rpm, at 10° C. for 10 minutes) and the 5FU content on the supernatant is determined.

The efficiency of encapsulation was determined indirectly on the supernatant by subtraction of the 5FU quantity out of the nanoparticles with respect to the loaded quantity. Then the samples were analysed by means of the HPLC-MS for determining the content of drug out of the nanoparticles.

$EE\% = $ drug weight in the $NP*100$/loaded drug weight.

Drug weight in the NP=loaded drug weight−drug weight in the supernatant.

The chemical-physical characterisation of the nanoparticles was realised by Zetasizer Nano ZS90 with the aim of determining the dimension and the surface load (mV) thereof, and the EE % analysis and Drug Loading of the systems loaded with the drug.

The efficiency of encapsulation of the drug was determined by HPLC-MS/MS analysis of the various samples obtained in the above-described experimental conditions.

To summarise, the efficiency of encapsulation was determined 1) indirectly on the supernatants by subtraction of the 5FU quantity out of the nanoparticles with respect to the loaded quantity; and 2) directly, following extraction of the drug from the nanoparticles isolated by centrifugation conducted at 1000 rpm at 4° C. for 15 minutes. The pellets were treated with 1 ml of MeOH and placed in an ultrasound bath for 20 minutes. The samples were analysed by means of the HPLC-MS for determining the content of drug. All the samples were diluted by a factor of 100.

TABLE III

| Batch | **Z-Ave (nm) | *PDI | Zeta potential (mV) | pH | wt % 5-FU/HSA |
|---|---|---|---|---|---|
| NP1HSA 10 | 123.3 ± 0.073 | 0.078 ± 0.020 | −44.4 ± 2.06 | 8.6 | 20 |
| NP1HSA 11 | 114.4 ± 0.404 | 0.146 ± 0.018 | −35.8 ± 2.11 | 8.6 | 40 |

TABLE III-continued

| Batch | **Z-Ave (nm) | *PDI | Zeta potential (mV) | pH | wt % 5-FU/HSA |
|---|---|---|---|---|---|
| NP1HSA 12 | 147.0 ± 1.637 | 0.275 ± 0.030 | −42.5 ± 0.153 | 10.0 | 40 |
| NP1HSA 10 bis | 120.5 ± 0.122 | 0.198 ± 0.056 | −43.4 ± 7.56 | 8.6 | 20 |
| NP1HSA 10 ter | — | — | — | 8.6 | 20 |
| NP1HSA 14 | — | — | — | 8.6 | 5 |

Summarising the results in table IV below:

TABLE IV

| Formulation | NOTES | EE % (wt %) | Drug Loading Mg/ml |
|---|---|---|---|
| NP1HSA 10 | 123.3 ± 0.073 | 7.4 | 102.3 |
| NP1HSA 11 | 114.4 ± 0.404 | | |
| NP1HSA 12 | 147.0 ± 1.637 | | |
| NP1HSA 10 bis* | 120.5 ± 0.122 | 20.9 | 190 |
| NP1HSA 10 ter | Not yet analyzed with Zetasizer | | |
| NP1HSA 14 | Not yet analyzed with Zetasizer | 12 | 73.4 |

*The sample has undergone an incubation time of 24 hrs at pH 8.6

The analyses were then concentrated on batches NP1HSA 10 ter, 11 and 12.

The results demonstrate that the incubation time is a determinant factor for the purposes of the increase in encapsulation efficiency.

In fact, the sample labelled batch NP1HSA10 bis prepared with an incubation time between Albumin and 5FU of 24 hours at pH 8.6 exhibits an EE % that is greater than all the samples analysed up to now.

In conclusion the method of the present invention enables obtaining HSA/5FU nanoparticles with an encapsulation efficiency of 20% and the nanoparticles contain a 5FU quantity of about 190 ug/ml.

Release Kinetics of the Drug

A simulation of parenteral administration of the NP1HSA10 bis sample (EE % 20.9 and drugloading 190 µg/ml) was analysed.

In particular, as a receiving step a PBS (phosphate buffered saline) at pH=7.4 was analysed. The method used is micro-dialysis by means of a system known as QuixSep® with a Spectra/pore membrane, MWCO=3500 Da.

The system was maintained under constant magnetic stirring, at ambient temperature, taking samples of the receiving step at predetermined times and re-integrating the collected volume.

A free drug dissolution experiment was also carried out (5FU solution in PBS at 200 µg/ml concentration).

The drug samples containing the 5FU were analysed both with the mass spectrometry method (LC-MS/MS) and with the spectrophotometry method UV-VIS at λ=265.0 nm.

The samples were analysed and the values obtained were plotted considering the single collections and re-integrations from the preceding step, so as to obtain a dissolution/release profile.

Figure 3:
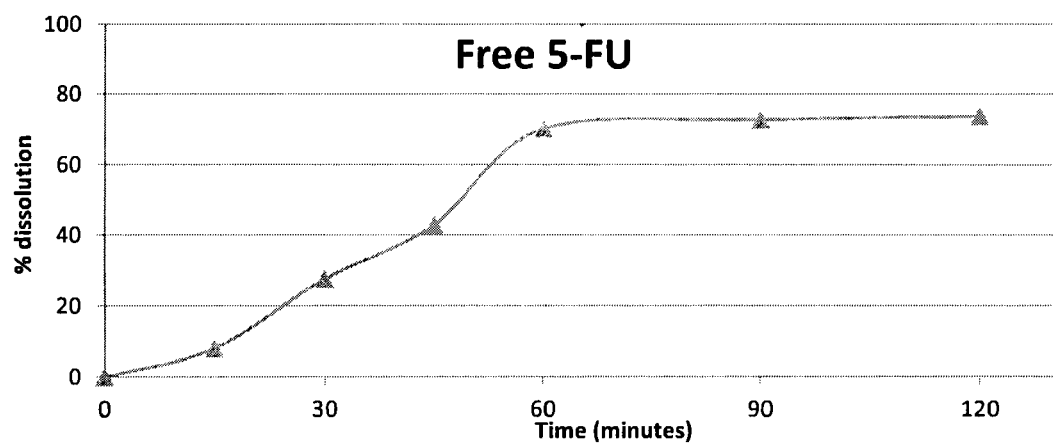
FIG. 3 shows the dissolution curves of the free drug in PBS (A) and the release curve of the 5FU incorporated in the albumin nanoparticles, i.e. the delivery system of the present invention (B).
Figure 3:
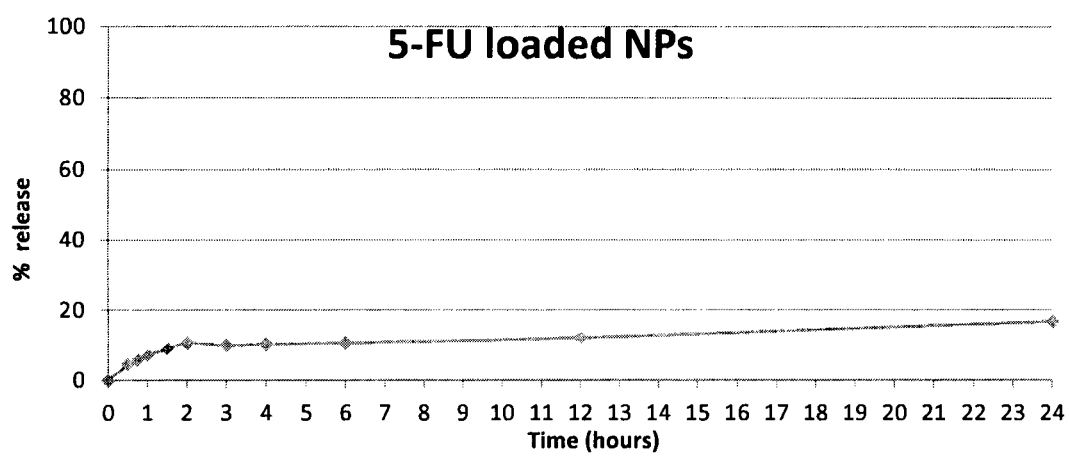

The results are reported in FIG. 3, which shows the dissolution curves of the free drug in PBS (A) and the release curve of the 5FU incorporated in the albumin nanoparticles.

The data relating to the release percentage were calculated on the basis of a drug loading determined by LC-MS/MS analysis.

The dissolution profile of the free drug has an increasing trend up to 60 minutes (5th point of FIG. 5A), reaching 70% of dissolution.

The process was monitored up to 2 hours (120 minutes).

In the case of the drug incorporated in the nanoparticles, the system releases growing quantities of drug up to 2 hours, then the release is constant over time, heading up at about 10% (FIG. 5B).

After 6 years a slight increase of the released percentage is observed, up to a maximum of 17%.

Briefly, the results demonstrate that the delivery system of 5FU, object of the invention, is able to constantly release, over the 24 hours, about 19 µg/ml of 5-FU.

The calculation was made considering a drugloading of 190 ug/ml and a release percentage of 10%.

This datum is very positive if we consider the fact that in the literature systems are known with a Cmax of about 50 µg/ml following administration of a bolus of 600 mg of 5FU, considering a body surface of 1.7. Further, it is stressed that in these conditions the plasmatic concentration of 5FU after 25 minutes becomes 10 µg/ml.

The invention claimed is:

1. A method for treating a tumour comprising a step of administering to an individual in need thereof an effective amount of nanoparticles of human serum albumin loaded with 5FU or a precursor thereof selected from among: capecitabine, UFT, S-1, dihydropyrimidine dehydrogenase inhibitors and folic acid, wherein:
   1) the quantity of 5FU or said precursor ranges from 10 to 500 µg/ml;
   2) the average diameter of the nanoparticles ranges from 80 to 180 nm;
   3) the weighted ratio between said 5FU and said human serum albumin is from 0.05 to 0.6;
   and wherein the nanoparticles release 5FU or the precursor at a constant quantity of about 10% for up to 24 hours or more.

2. The method according to claim 1, wherein the tumour is selected from among: colon carcinoma, rectal carcinoma, gastric adenocarcinoma, head/neck tumour, hepatic carcinoma, pancreatic carcinoma, peritoneal carcinomatosis, oesophageal carcinoma, breast carcinoma, ovarian carcinoma, microcytoma lung tumour, non-microcytoma lung tumour, non-invasive surface carcinoma of the bladder, Kaposi's sarcoma, and sarcoma of the soft tissues, preferably the tumour being selected from among: colon carcinoma, rectal carcinoma, gastric adenocarcinoma, pancreatic carcinoma, breast carcinoma, microcytoma lung tumour, non-microcytoma lung tumour, non-invasive surface carcinoma of the bladder.

3. The method according to claim 1 wherein said nanoparticles are parenterally administered.

4. The method according to claim 1 wherein said nanoparticles are administered intravenously.

5. The method according to claim 1 wherein said nanoparticles are administered via bolus.

6. The method according to claim 1 wherein said nanoparticles is administered in combination with administration of at least a chemotherapy agent, with radiotherapy, with surgery, or a combination thereof.

7. The method according to claim 1, wherein the efficiency of release of 5FU or the precursor is about 10% of the quantity of loaded drug.

8. The method according to claim 1, wherein the quantity of 5FU or the precursor released constantly by the nanoparticles is about 10-50 µg/ml.

9. The method according to claim 8, wherein the quantity of 5FU or the precursor released constantly by the nanoparticles is about 15-30 µg/ml.

10. The method according to claim 8, wherein the quantity of 5FU or the precursor released constantly by the nanoparticles is about 17-22 µg/ml.

\* \* \* \* \*